United States Patent [19]

Lawless et al.

[11] Patent Number: 5,718,562

[45] Date of Patent: Feb. 17, 1998

[54] INTERFACE MODULE FOR USE WITH AN NCT-BASED PUMPING MECHANISM AND NCT-BASED CASSETTE

[75] Inventors: Michael W. Lawless, Poway; Ashok Kaul, San Diego, both of Calif.; Gregory G. Hoerner, Carolina, Puerto Rico

[73] Assignee: Abbott Laboratories, Abbott Park, Ill.

[21] Appl. No.: 551,973

[22] Filed: Nov. 2, 1995

[51] Int. Cl.⁶ .................................................. F04B 49/00
[52] U.S. Cl. ........................... 417/1; 604/19; 439/909; 417/53; 361/730
[58] Field of Search .......................... 417/1, 53, 44.1, 417/44.2, 360; 604/19, 27, 30–31, 44, 151, 67; 128/DIG. 12, DIG. 13; 307/64; 361/679, 728–730; 439/283, 882, 909, 957

[56] References Cited

U.S. PATENT DOCUMENTS

| | | | |
|---|---|---|---|
| 4,084,214 | 4/1978 | Eppich | 361/394 |
| 4,719,696 | 1/1988 | Castner | 29/830 |
| 4,756,706 | 7/1988 | Kerns et al. | 604/66 |
| 5,104,374 | 4/1992 | Bishko et al. | 604/31 |
| 5,368,562 | 11/1994 | Blomquist et al. | 604/65 |
| 5,370,622 | 12/1994 | Livingston et al. | 604/151 |
| 5,371,687 | 12/1994 | Holmes, II et al. | 364/514 |
| 5,601,445 | 2/1997 | Schipper et al. | 439/341 |
| 5,628,619 | 5/1997 | Wilson | 417/44.2 |
| 5,630,710 | 5/1997 | Tune et al. | 417/326 |
| 5,647,854 | 7/1997 | Olsen et al. | 604/174 |

*Primary Examiner*—Timothy Thorpe
*Assistant Examiner*—Xuan M. Thai
*Attorney, Agent, or Firm*—Neal D. Marcus

[57] ABSTRACT

A modular ambulatory infusion pump comprises a base unit including an integral housing, said base unit including an infusion pump for infusing fluid into a patient's body, a battery power supply for energizing infusion pump and a control for operating the infusion pump to achieve at least one of a desired rate, a desired volume and a desired time interval for infusing the fluid. Disposed on the integral housing is a first electrical connector, said first electrical connector being provided to electrically couple the base unit to a mating connector on one of the plurality of modules, said one of the plurality of modules being coupled to the base unit to add a selected additional port to the base unit and to provide additional capability, said plurality of modules including a data port module that includes a printer interface port. Also provided is an external power input module that includes a power port for coupling the modular ambulatory infusion pump to an AC line to provide electrical power for the base unit.

11 Claims, 4 Drawing Sheets

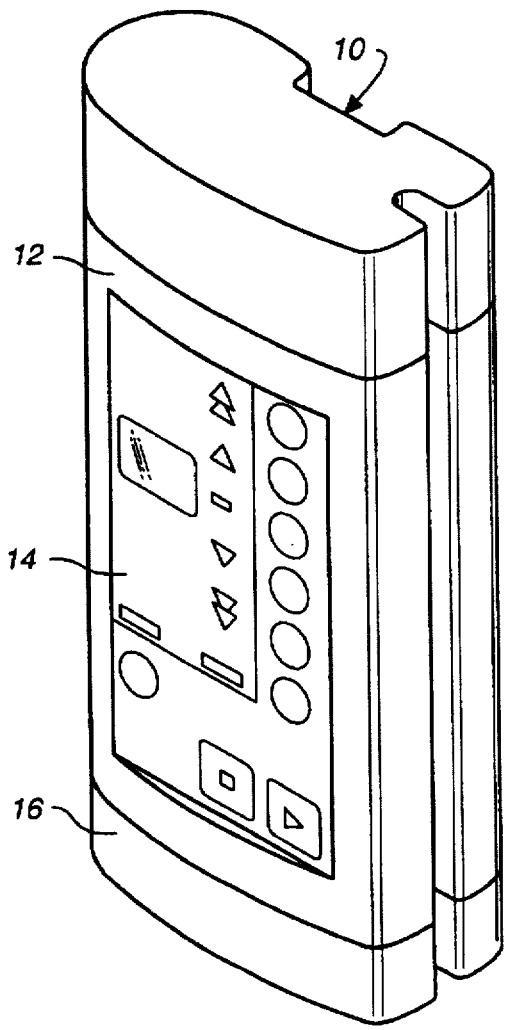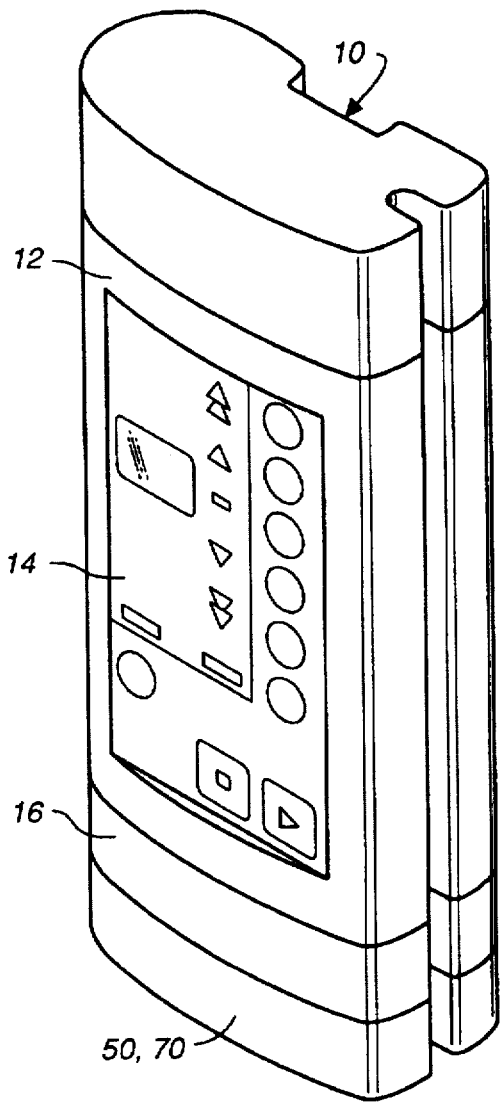
FIG._1       FIG._5

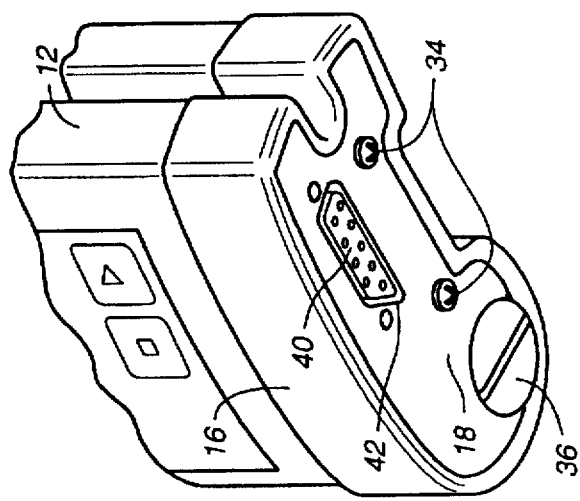
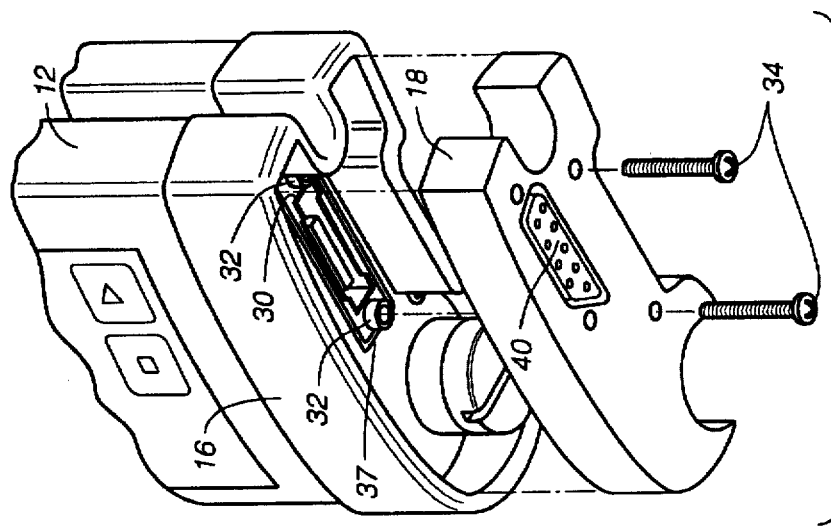
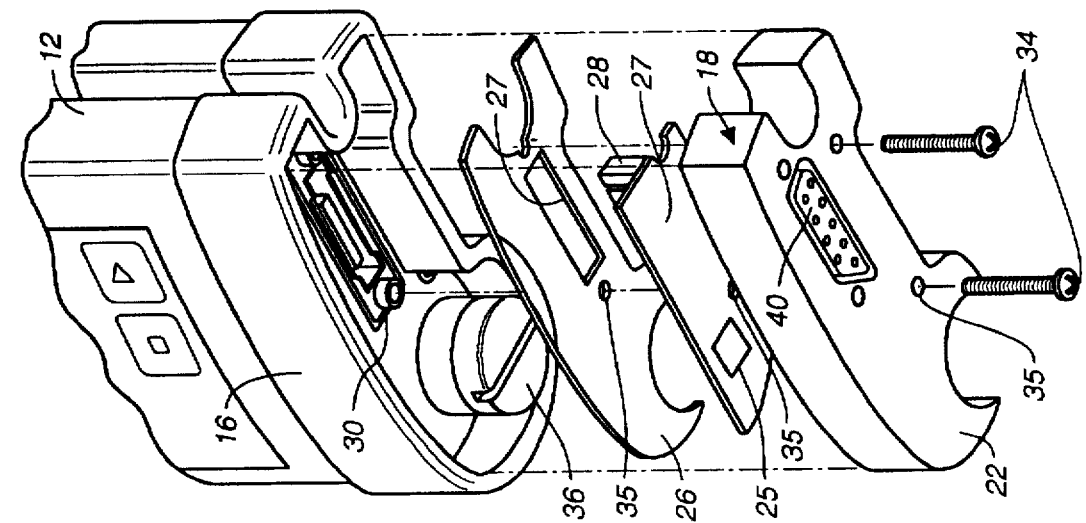

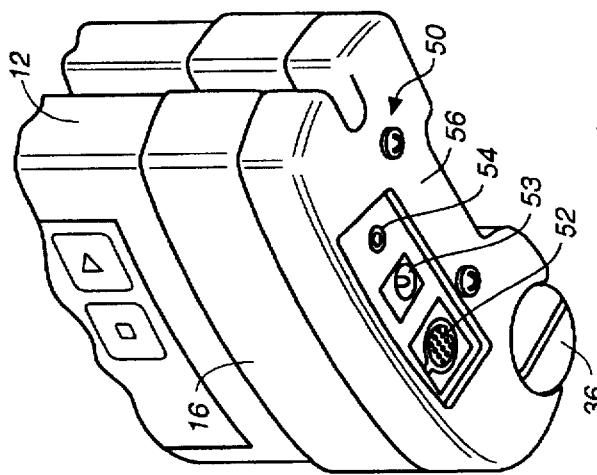
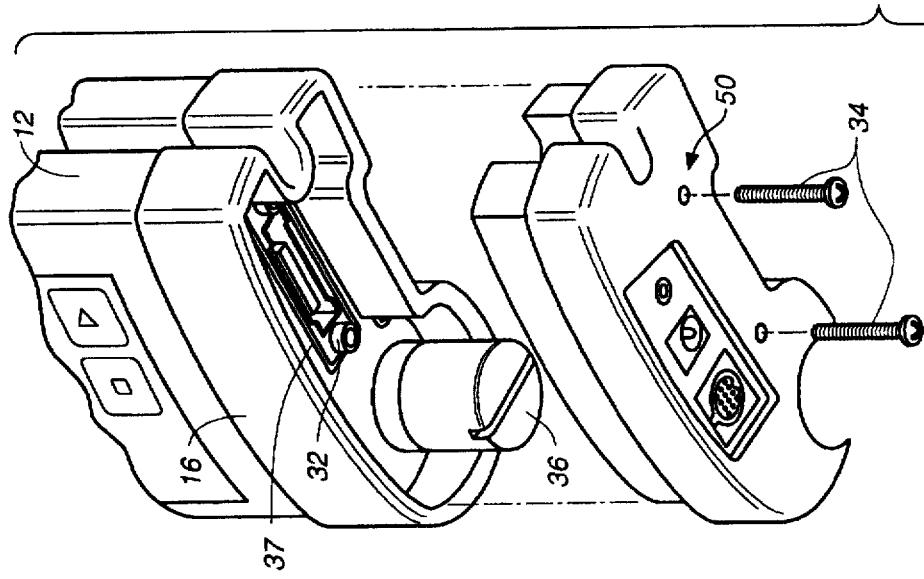
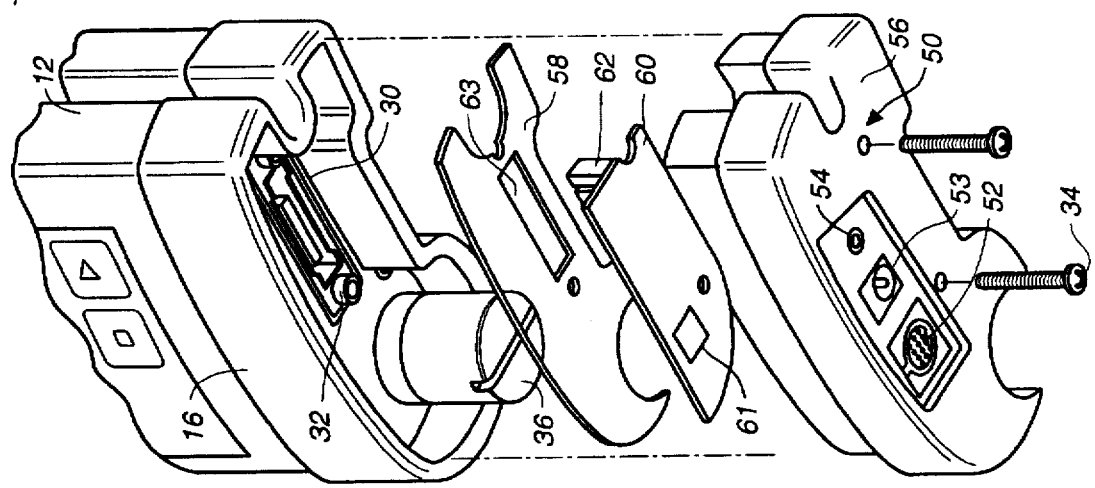

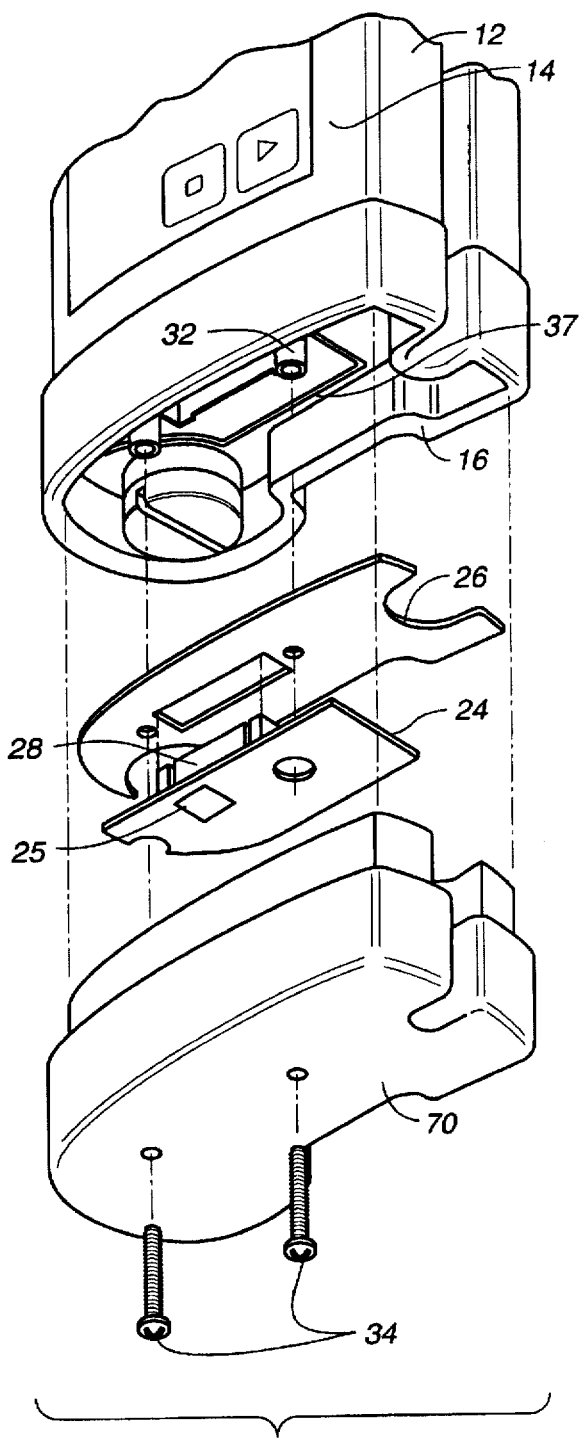
FIG._9
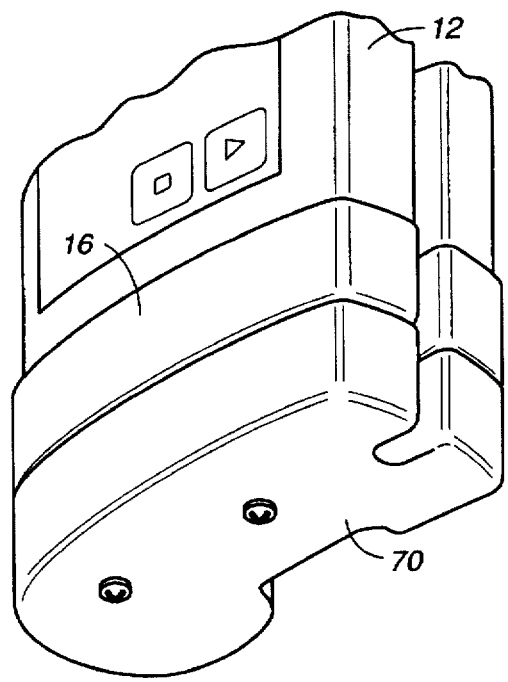
FIG._10

INTERFACE MODULE FOR USE WITH AN NCT-BASED PUMPING MECHANISM AND NCT-BASED CASSETTE

FIELD OF THE INVENTION

The present invention relates generally to ambulatory drug infusion pumps and methods for operating such pumps. In particular, the present invention relates to a system for integrating multiple pump functions and multiple pump interface functions into at least one mutually aligned modules.

BACKGROUND OF THE INVENTION

In recent years there has been an increase in use of positive displacement fluid infusion pumping devices for delivery of medical fluids intravenously or intra-arterially to patients in hospitals or other patient care locations. Such pumps are desirable due to their much greater accuracy and delivery rates in dosages, the relative sophistication in permitting a flexible and controlled feed from multiple fluid sources, and particularly their ability to control with precision the amount of potent drugs delivered to a patient over a given period of time.

It has been found conventional injection techniques rarely produce a maximum therapeutic value for certain drugs. The full therapeutic potential of many drugs can only be reached through precise delivery over an extended of time. One example is the use of insulin therapy in the treatment of diabetes. Many diabetics cannot adequately control their insulin requirements through a single daily injection, or even multiple daily insertions, of insulin. However, such patients can use a portable drug delivery system to deliver a controlled measure of insulin over an extended period of time and achieve successful and satisfactory treatment of their diabetic condition.

Moreover, the current climate in the health care industry is requiring many patients to undertake drug therapy on an outpatient basis, using an ambulatory infusion pump. For example, it is desirable to use such portable infusion pumps for chemotherapy, pain management, enteral feeding, and other significant health care applications.

However, each healthcare application has its own unique requirements associated with drug or medical fluid delivery. For example, a pain management regimen might require bolus delivery of a pain controlling drug, a diabetic might require a continuous low dose of insulin and enteral feeding might require intermittent delivery on a pre-set feeding schedule of a medical fluid of considerably different consistency than either of the aforementioned medical applications.

Previously it was found that to fulfill the requirements of such diverse medical infusion procedures required a variety of pumps to deal with the varying conditions of each of these procedures. Some pumps would have to be used over a period of time for a variety of therapies such as those described above, for the same or different patients. Moreover, pumps were defined by therapy type such as chemotherapy, pain management, enteral feeding, antibiotic treatment, et al.

That is, a pain management regimen required a pain management pump, a chemotherapy regimen required a chemotherapy pump, and so forth. Typically, a pain management pump was not suitable to provide chemotherapy treatment or extended drug infusion such as required for insulin treatment. However, hospitals have required that substantial changes be made in the medical industry's approach to pump development. There is a substantial desire within the hospital environment to reduce the inventory of pumps used for treatment by the provision of pumps having multiple tasking abilities.

One example of such an approach is disclosed in U.S. Pat. No. 4,756,706 wherein a modular system is provided in which a central pump and a separate monitoring modules can be selectively attached, both physically and electrically to a central management unit. The central management unit controls the setup of all the modules attached to it and receives and displays information from them.

Each of the modules, however, is capable of being detached from the central management unit, and while so detached is capable of operating independently for an extended period of time. During this period, the detached unit internally maintains records which assure an accurate display once it is reattached to the central management unit.

However, such configurations envision multi-tasking systems capable of treating of multiplicity of patients in a hospital setting utilizing such diverse parameters as pulse oximetry, drug infusion, oximetry, and other necessary but unrelated parameters. Such a system is not readily adapted to an ambulatory device having the same need for diverse therapies to be performed by a single pump. There is an increasing need for sophisticated drug delivery systems associated with ambulatory infusion pumps.

An alternate approach as set forth in U.S. Pat. No. 5,368,562 discloses an infusion pump system for dispensing a drug to a patient including: a set of memory modules, each memory module containing information defining a specific user interface; a housing with memory access structure for replaceably accepting one of the memory modules; a reservoir mounted on the housing for holding a drug; a drug delivery system for delivering the drug from the reservoir to the patient; and a drug delivery system mounted in the housing for operating the drug delivery system.

The delivery control system includes a microprocessor coupled to one memory module. The microprocessor receives the information from the memory module to operate the delivery system in conformance with the specific user interface as defined by the information in the memory module. However, there is a need to advance the technology to develop specific memory modules to be incorporated in a drug delivery system to include further desirable features to an ambulatory drug infusion pump.

SUMMARY OF THE INVENTION

The present invention envisions an advance over the modular concept of the '562 patent in that the present invention incorporates power auxiliary features within individual modules such as a data port module which includes a printer interface port or an external power input module which includes a power port for coupling a modular ambulatory infusion pump to a AC line to provide electrical power for a base unit. Moreover, it is envisioned that such power accessory modules be microprocessor driven to provide additional selectivity and control for each of these associated power modules.

In accordance with the present invention, a modular ambulatory infusion pump comprises a base unit including an integral housing, said base unit including an infusion pump for infusing fluid into a patient, a battery power supply for energizing infusion pump and a control for operating the infusion pump to achieve at least one of a desired rate, a desired volume and a desired time interval for infusing the fluid.

Disposed on the integral housing is a first electrical connector, said first electrical connector being provided to electrically couple the base unit to a mating connector on one of the plurality of modules, said one of the plurality of modules being coupled to the base unit to add a selected additional port to the base unit and to provide additional capability, said plurality of modules including a data port module that includes a printer interface port. Also provided is an external power input module that includes a power port for coupling the modular ambulatory infusion pump to an AC line to provide electrical power for the base unit.

Moreover, it is envisioned that the present invention provide a modular ambulatory infusion pump which is water resistant, which base unit includes an infusion pump for infusing the fluid into the patient's body, an integral housing enclosing the drug infusion pump, a housing seal, a battery power supply for supplying electrical power to energize the infusion pump, and a control for operating the infusion pump. A first electrical control disposed on the integral housing is provided to electrically couple the base unit to a mating connector disposed on one of the plurality of modules, each of the plurality of modules and each mating connector on each module being sealed to prevent water from entering the module while the modules are electrically coupled to the base unit, so that the base unit and the module coupled thereto are not damaged by exposure to water, e.g., when the pump is worn by the patient while bathing.

The present invention is better understood by consideration of the detailed description set forth below particularly when such detailed description is considered in conjunction with the drawings which accompany the subject specification.

BRIEF DESCRIPTION OF THE DRAWINGS

FIG. 1 is a front right perspective view of an ambulatory infusion pump incorporating a new single function interface module of the present invention disposed in the end cap of the pump housing;

FIG. 2 is an exploded perspective view of the lower end of the pump of FIG. 1 in which a firmware module is separated therefrom and the components of such module are also separated;

FIG. 3 is an exploded perspective view in which the firmware module of FIG. 1 is separated from the lower end of the pump;

FIG. 4 is a perspective view of the lower end of the pump of FIG. 1 showing the firmware module of FIG. 3 mounted in place on the lower end of the pump;

FIG. 5 is a front, right perspective view of an ambulatory infusion pump in which a multi-function module of the present invention is mounted in the end cap of the pump;

FIG. 6 is an exploded perspective view of the lower end of the pump of FIG. 5 in which the multi-function module is separated from the lower end of the ambulatory drug infusion pump and the components of such module are also separated;

FIG. 7 is an exploded perspective view in which the assembled multi-function module of FIG. 5 is separated from the lower end of the pump;

FIG. 8 is a view similar to FIG. 6 in which the multi-function module is mounted on the lower end of the pump;

FIG. 9 is an exploded perspective view showing an optional battery module, with the module also shown in an exploded view, to display the components thereof, for mounting at the lower end of the ambulatory drug infusion pump; and FIG. 10 is a view in which the assembled battery module is joined to the pump at the lower end thereof.

DETAILED DESCRIPTION

The drug infusion pump 10 shown in FIG. 1 is a relatively small drug infusion pump intended for ambulatory usage in which a clip (not shown) mounted at the back of the pump enables the user to mount the pump 10 over a belt or other clothing worn by the patient. The drug infusion pump 10 includes an integral housing 12 and a user interface 14 which enables the user of the pump to input information related to a desired parameter for infusion drugs such as at least one of a desired rate, a desired volume, or a desired time interval for infusing the drug. Disposed at the lower end of the housing is an end cap 16. The housing 14 is integrally molded, to be water-tight, with the housing and user interface 14 junction also water-tight.

As shown in the exploded perspective view of FIG. 2, the end cap 16 comprises an elastomeric shell molded over a rigid inner plate. Disposed at the bottom of the pump 10 within the end cap 16 is a firmware module 18. The module 18 includes a base 22, a printed circuit board 24 and a cover 26. The printed circuit board 24 enables a cable input 40 for a printer (not shown). Other functions could also be provided by the circuit board 24 for the module 18, such as an a/c power adaptor, a bolus jack, or a phone jack to transmit pump data to a remote location.

Also carried on the printed circuit board is a microprocessor 25 and an input/output connector 28. Microprocesser 25 may be a 6805 Microprocessor manufactured by Motorola, or similar which may be used to change the language of use for the pump, e.g., English to French, or change the pump protocol, e.g., pain management to enteral feeding. When the firmware module 18 is fully assembled, the printed circuit board 24 is reposed within the base 22. The printed circuit board 24, carrying on an upper surface the input/output connector 28, reposes within the base 22 with the cover 26, having an opening 27 through which the input/output connector protrudes when the cover is secured in place to enclose the module 18 as shown in FIG. 3.

A complementary input/output connector 30 is disposed within the pump end cap 16 at the lower end of the pump housing 12. Note that provided at the opposite ends of the input/output connector 30 disposed on the pump housing 12 are threaded members 32, which engage jack screws 34, which pass through aligned openings 35 in the base 22, the printed circuit board 24 and the cover 26 to engage threaded members 32 to draw the assembled firmware module 18 into the end cap 16 of the pump 10.

Disposed within the end cap 16 is a battery cap 36 at one edge portion thereof, the battery cap providing access to a battery holding chamber (not shown) of the pump 10. Further the firmware module 18 is shaped to conform generally to the shape of the volume defined by the pump end cap 16 including the battery cap 36.

In FIG. 3 the firmware module 18 is shown fully assembled and aligned generally with the volume defined within the pump end cap 16 to align respective module input/output connector 28 and pump input/output connector 30 for insertion of the firmware module 18 into the end cap 16. The input/output connector 30 associated with the pump end cap 16 includes a compliant elastomeric seal 37 disposed around the periphery of the connector 30 to define a peripheral ridge which forms a watertight seal around the respective connectors 28 and 30 when the jack screws 34 are received in the threaded members 32 to draw firmware module 18 up into the end cap 16.

In FIG. 4, the module 18 is shown completely disposed within the end cap 16 with the battery cap 36 at one end. In the fully assembled position of FIG. 4, a printer cable jack 40 is disposed at the base of the firmware module 18 and is electrically connected to input/output connector 28 in the upper end of the module 18 which is received into the input/output connector 30 of the housing 12.

An alternative pump module configuration is shown in FIGS. 5 through 8 wherein the pump 10 is fitted with a multi-function firmware module 50. The multi-function firmware module 50 includes at a bottom face multiple input/output ports such as a printer port 52, an a/c adapter 53 and a bolus jack 54. However, the port can be modified to include alternative functions, such as a phone jack.

The multi-function module 50 is comparable to the module 18 in that it includes a base 56 and a cover 58. Disposed within the module 50 is a printed circuit board 60 having a microprocessor 61, and, at an upper end thereof, an input/output connector 62. When the module 50 is assembled the printed circuit board 60 is placed within the base 56, then the cover 58 is put in place with an opening 63 therein allowing the input/output connector 62 of the module to extend therethrough.

The module 50 is fully compatible with the end cap 16, the input/output connector 30 of the pump housing 12, threaded fasteners 32 associated with the input/output connector 30 and the battery cap 36. Shown in FIG. 7 the module 50 is fully assembled and prepared to be inserted into the end cap 16. When the module 50 is secured to the housing 12, compliant peripheral member 37 forms a water-tight seal around the connectors 30, 62 and jack screws 34 mounted on the lower face of the module 50 are tightened to secure the module to the lower end of housing 12 of pump 10.

An assembly incorporating an optional battery module 70 is shown in FIG. 9 and 10. In the exploded view of FIG. 9 the battery firmware module 70 is shown to include a printed circuit board 24, a microprocessor 25, input/output connector 28, and a cover 26. The battery module 70 can be assembled and then inserted into end cap 16 of the pump body in the same manner as modules 18 and 50.

While the present invention has been disclosed with respect to a preferred embodiment those of ordinary skill in the art will understand that further modifications may be made within the scope of the claims that follow. Accordingly, it is not intended that the claims in any way be limited by the disclosure of the preferred embodiment, but that the scope of the invention be determined solely by reference to the claims.

The embodiment of the invention in which an exclusive property or privilege is claimed is defined as follows:

We claim:

1. A modular ambulatory infusion pump, comprising:
   a base unit including an integral housing, said base unit including an infusion pump for infusing a fluid into a patient's body, a battery power supply for energizing the infusion pump, and a control for operating the infusion pump to achieve at least one of a desired rate, a desired volume, and a desired time interval for infusing the fluid;
   a first electrical connector disposed on the integral housing, said first electrical connector being provided to electrically couple the base unit to a mating connector on one of a plurality of modules, said one of the plurality of modules being coupled to the base unit to add a selected additional port to the base unit and to provide additional capability, said plurality of modules including a data port module that includes a printer interface port, and an external power input module that includes a power port for coupling the modular ambulatory infusion pump to an AC line to provide electrical power for the base unit.

2. A modular ambulatory infusion pump as claimed in claim 1 wherein said plurality of modules includes a bolus port module to enable bolus delivery by the pump.

3. A modular ambulatory infusion pump as claimed in claim 1 wherein the plurality of modules includes a phone port module that enables delivery of pump data to a remote location over a phone line.

4. A modular ambulatory infusion pump as claimed in claim 1 wherein each of said plurality of modules includes a microprocessor operable to change the operating language of the pump and/or the pump protocol.

5. A modular ambulatory infusion pump as claimed in claim 1 wherein each of said plurality of modules includes at least a base, a printed circuit board disposed in the base and a cover overlying the printed circuit board.

6. A modular ambulatory infusion pump as claimed in claim 5 wherein a battery cap is disposed in the pump at lower end thereof, and the module disposed in the pump is shaped to accommodate the battery cap.

7. A modular ambulatory infusion pump that is water resistant, enabling a patient receiving medication by infusion from the pump to bathe while the infusion pump is in use without causing damage to the infusion pump due to exposure of the infusion pump to water, comprising:
   a base unit including an integral housing sealed to prevent water from entering the integral housing, said base unit including within the integral housing an infusion pump for infusing a fluid into a patient's body, a battery power supply for supplying electrical power to energize the infusion pump, and a control for operating the infusion pump;
   a first electrical connector disposed on the integral housing, said first electrical connector being provided to electrically couple the base unit to a mating connector disposed on one of a plurality of modules, each of said plurality of modules and the mating connector on said modules being sealed to prevent water entering the module while the module is electrically coupled to the base unit, so that the base unit and module are not damaged by exposure to water during bathing by the patient.

8. A modular ambulatory infusion pump that is water resistant as claimed in claim 7 wherein the first electrical connector disposed on the integral housing is surrounded by a compliant waterproof seal, and the module includes aligned fasteners which engage complementary threaded members provided on the housing so that when the fasteners passing through the module engage the threaded members on the housing an upper face on the module is drawn into water tight engagement with the compliant seal on the housing to assure a water resistant interface between the pump and the module.

9. A modular ambulatory infusion pump, comprising:
   a base unit including an integral housing, said base unit including an infusion pump for infusing a fluid into a patient's body, a battery power supply for energizing the infusion pump, and a control for operating the infusion pump to achieve at least one of a desired rate, a desired volume, and a desired time interval for infusing the fluid;
   a first electrical connector disposed on the integral housing, said first electrical connector being provided to electrically couple the base unit to a mating connector on one of a plurality of modules, said one of the plurality of modules being coupled to the base unit to add a selected additional port to the base unit and to provide additional capability, at least one of said modules including a plurality of data ports which comprises a printer interface port, a power port for coupling the modular ambulatory infusion pump to an AC line to provide electrical power for the base unit, and a bolus port for enabling bolus delivery by the pump.

10. A method of enabling a modular ambulatory infusion pump to deliver and receive data from multiple pump interfaces, the method comprising:

the step of providing a base unit including an integral housing, said base unit including an infusion pump for infusing a fluid into a patient's body, a battery power supply for energizing the infusion pump, and a control for operating the infusion pump to achieve at least one of a desired rate, a desired volume, and a desired time interval for infusing the fluid;

the step of providing a first electrical connector disposed on the integral housing;

the step of electrically coupling the base unit to a mating connector on one of a plurality of modules, said one of the plurality of modules being coupled to the base unit to add a selected additional port to the base unit and to provide additional capability; and the step of including in said plurality of modules a data port module that includes a printer interface port, and an external power input module that includes a power port for coupling the modular ambulatory infusion pump to an AC line to provide electrical power for the base unit.

11. A method of making a modular ambulatory infusion pump water resistant, enabling a patient receiving medication by infusion from the pump to bathe while the infusion pump is in use without causing damage to the infusion pump due to exposure of the infusion pump to water, the method comprising:

the step of providing a base unit including an integral housing sealed to prevent water from entering the integral housing, said base unit including within the integral housing an infusion pump for infusing a fluid into a patient's body, a battery power supply for supplying electrical power to energize the infusion pump, and a control for operating the infusion pump;

the step of disposing a first electrical connector on the integral housing to electrically couple the base unit to a mating connector disposed on one of a plurality of modules; and the step of sealing each of said plurality of modules and the mating connector on said modules to prevent water entering the module while the module is electrically coupled to the base unit, so that the base unit and module are not damaged by exposure to water during bathing by the patient.

\* \* \* \* \*